United States Patent [19]

Breiner et al.

[11] Patent Number: 4,834,862
[45] Date of Patent: May 30, 1989

[54] AMPHOLYTE SEPARATION METHOD AND APPARATUS

[75] Inventors: Steven J. Breiner; Charles H. Lochmuller, both of Durham, N.C.

[73] Assignee: Duke University, Durham, N.C.

[21] Appl. No.: 243,329

[22] Filed: Sep. 12, 1988

[51] Int. Cl.[4] ..................... G01N 27/28; G01N 27/26; G01N 27/40

[52] U.S. Cl. ................. 204/301; 204/299 R; 204/183.2

[58] Field of Search ............... 204/183.2, 299 R, 301, 204/182.3, 182.9, 180.1

[56] References Cited

U.S. PATENT DOCUMENTS

| | | | |
|---|---|---|---|
| 3,240,692 | 3/1966 | Donnelly | 204/182.3 |
| 3,287,244 | 11/1966 | Mel | 204/182.3 |
| 3,330,749 | 7/1967 | Kuwata et al. | 204/182.6 |
| 3,506,554 | 4/1970 | Broome | 204/299 R |
| 3,664,939 | 5/1972 | Lumer et al. | 204/183.2 |
| 3,692,654 | 9/1972 | Svendsen | 204/183.3 |
| 3,758,395 | 9/1973 | Strickler | 204/183.2 |
| 3,773,645 | 11/1973 | Nees et al. | 204/299 R |
| 3,829,370 | 8/1974 | Bourat | 204/182.1 |
| 3,870,617 | 3/1975 | Bourat | 204/301 |
| 3,962,058 | 6/1976 | Denckla | 204/299 R |
| 4,204,929 | 5/1980 | Bier | 204/182.3 |
| 4,234,404 | 11/1980 | Satoh | 204/299 R |
| 4,289,596 | 9/1981 | Satoh | 204/180.1 |
| 4,309,268 | 1/1982 | Richman | 204/301 |
| 4,315,812 | 2/1982 | Karlson | 204/299 R |
| 4,362,612 | 12/1982 | Bier | 204/301 |
| 4,396,477 | 8/1983 | Jain | 204/182.1 |
| 4,401,538 | 8/1983 | Hausfeld | 204/182.4 |
| 4,441,978 | 4/1984 | Jain | 204/301 |
| 4,533,447 | 8/1985 | Meldon | 204/181.4 |
| 4,670,119 | 6/1987 | Hurd | 204/183.2 |

OTHER PUBLICATIONS

Publication by Luner et al., *Proceedings of the National Academy of Sciences*, vol. 66, No. 3, pp. 898–903 (1970) entitled "A New Approach to Isoelectric Focusing and Fractionation of Proteins in a pH Gradient".

Publication by Lundahl et al., *Annals New York Academy of Sciences*, vol. 209, No. 94, pp. 94–111 (1973) entitled "Isoelectric Focusing in Free Ampholine Solution and Attempts at Isoelectric Focusing in pH Gradients Created in Ordinary Buffers".

Publication by Janca et al., *Analytical Chemistry*, vol. 56, No. 13, pp. 2481–2484 (1984) Entitled "Focusing in Field-Flow Fractionation".

Primary Examiner—John F. Niebling
Assistant Examiner—John S. Starsiak, Jr.
Attorney, Agent, or Firm—Richard E. Jenkins

[57] ABSTRACT

An ampholyte separation apparatus and method which utilize a thermally engendered pH gradient to separate amphoteric molecules according to their isoelectric points and/or mobilities. Two independently temperature controllable thermal masses located on opposing ends of a plurality of barriers situated transverse to a flow channel create a pH gradient along the length of the transverse barriers. A pair of electrodes create an electric field along the length of the transverse barriers so as to cause ampholytes traveling down the flow channel to migrate into the transverse barriers and stabilize at points corresponding to their isoelectric points. Alteration of the pH gradient causes the separated amphoteric molecules to reenter the flow stream at different times and to be separately eluted and collected.

27 Claims, 3 Drawing Sheets

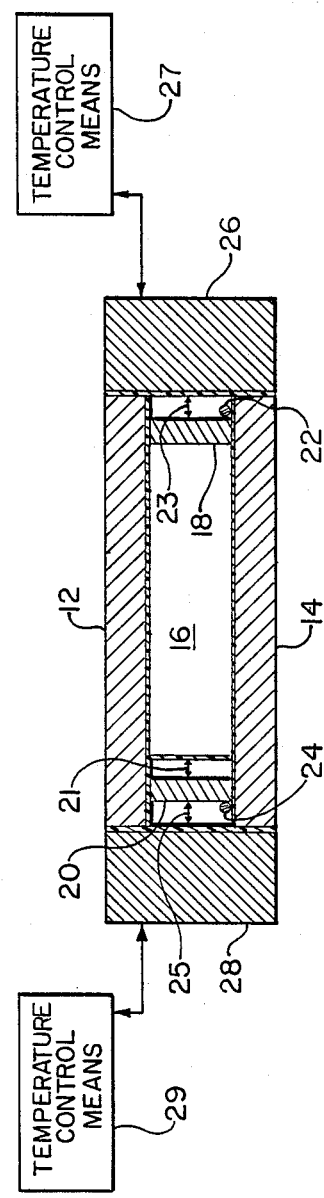

AMPHOLYTE SEPARATION METHOD AND APPARATUS

DESCRIPTION

1. Technical Field

This invention relates to the separation of biological materials and more specifically, to an ampholyte separation method and apparatus wherein a novel arrangement of a flow channel transverse barriers and electrodes are utilized with a readily controllable pH gradient to provide for the efficient separation of ampholytes having varying isoelectric points.

2. Background Art

The separation of biological materials from their natural environment is becoming increasingly important in light of the current advancements being made in biotechnology and related fields. Separation and purification techniques are especially important since the effectiveness of biological materials, such as proteins, is frequently dependent on the purity with which the material may be isolated.

Amphoteric biological materials, commonly known as ampholytes, maintain a positive charge in acidic media nd a negative charge in basic media. Each ampholyte has a characteristic isoelectric point which corresponds to the pH at which the ampholyte has a zero net charge. In the presence of a pH gradient and an electric field, an ampholyte will migrate electrophoretically to a position within the pH gradient where the net charge of the molecule is zero. Traditional isoelectric focusing (IEF) techniques utilize an established pH gradient and an electric field so as to focus the ampholyte into zones defined by the pH of the medium and the electric field applied.

For example, U.S. Pat. No. 4,204,929 describes an isoelectric focusing method whereby the fluid to be separated is pumped through generally parallel channels which are composed of permeable microporous membranes. The fluid is pumped in a direction parallel to the permeable channels and an electrical potential is applied across the streamlined channels. A pH gradient is established across the channels such that the electrical field causes various ampholytes to flow through the membranes of the separating channels and eventually migrate to the channel corresponding to the pH of the isoelectric point of each ampholyte. The fluid in each of the streamlined channels is recirculated such that the fluid flowing out of each channel is recirculated back to the entrance of the channel. The fluids are also cooled in the process of recirculation so as to minimize problems with dissipation of Joulian heat during isoelectric focusing.

A horizontal isoelectric focusing apparatus is described in U.S. Pat. No. 4,234,404. The apparatus includes a hollow elongated electrophoresis vessel which has an electrode at each opposite end. An unobstructed zone is provided in the interior of the vessel and is located at the bottom of the vessel when the vessel is in the normal position for electrophoresis. Located above the unobstructed zone are a plurality of upright, parallel, horizontally spaced partitions defining isolated compartments. The separation is carried out by depositing the fluid to be separated into the vessel such that it forms a liquid layer in the unobstructed zone. An electric potential is applied across the electrodes so that the components of the fluid migrate horizontally due to their different electrophoretic mobilities and eventually stabilize corresponding to their isoelectric points. The electric potential is then discontinued and the vessel is rotated about its horizontal longitudinal axis so as to bring the partitions into contact with the fluid layer. The respective fractions of separated components are thereby captured within isolated compartments and can then be recovered from the vessel.

An isoelectric focusing method and apparatus are also described in U.S. Pat. No. 4,670,119. The IEF device includes a series of parallel electrodes located around the border of a focusing chamber. The voltages of the electrodes may be controlled by the user so as to maintain various voltages along the length of the chamber. The ionic species present in the buffer solution will be concentrated at either the anode or cathode end of the chamber. The resulting charge imbalance will cause the dissociation of water thereby establishing a pH gradient. This technique allows the formation of a wide range of pH gradients, and the gradient may be altered during the isoelectric focusing process without disturbing the components being separated.

Also of interest, an apparatus for continuous electrochromatographic separation is described in U.S. Pat. No. 4,315,812. A vertical sandwich of rectangular glass containing a filter material is provided and a sample to be separated is pumped into the top of the vertical chamber such that the fluid flows under the force of gravity through the chromatographic column. Simultaneously, an electric field is applied across the fluid path such that the charged molecules migrate horizontally according to their respective electrophoretic mobilities. Therefore, instead of the fluid sample traveling down the column in a single path, the electric field causes the fluid to separate into different bands of components which travel vertically in separate paths. The separate samples can then be collected along the lower edge of the glass sandwich.

In general, isoelectric focusing techniques are disadvantageous in that prefocusing of the pH gradients typically requires several hours of tedious preparation. The long preparation times required further prolong the already lengthy IEF separation process. Additionally, the gels and other materials utilized to stabilize the pH gradient create difficulties in detecting and recovering the separated ampholytes.

Field-flow fractionation (FFF) is a method for separating particles according to size and is based on the differential flow profile through a channel. The particles are concentrated by an applied force (e.g., electric, magnetic, thermal, centrifugal, etc.) in various regions of the flow and will travel through the channel at different speeds thus being eluted at varying times. However, FFF techniques have been limited to analyses of small samples by the fact that the separation channels used are necessarily of small dimension in the direction of fractionation in order to maintain the differential flow profiles needed.

A need therefore exists for a method and apparatus for separating amphoteric species that utilizes a readily established and controllable pH gradient and that will facilitate the detection and recovery of the separated ampholyte molecules. The novel procedure and corresponding apparatus described herein should solve many of the problems associated with presently existing isoelectric focusing and field-flow fractionation techniques.

DISCLOSURE OF THE INVENTION

The separation apparatus of the present invention comprises a flow channel and a series of evenly and closely-spaced channels positioned transversely to the flow channel. Two electrodes are positioned along the length of the separation apparatus so that one is adjacent each of the outside ends of the closely-spaced channels and the other electrode is spaced-apart from the inside ends of the channels and positioned adjacent the flow channel. A thermal mass is located adjacent to each of the electrode compartments and extends along the length of the separation apparatus. Semipermeable membranes separate the electrode compartments from the sample flow channel and the closely-spaced transverse channels. A bottom plate and a top plate enclose the apparatus so as to create a fluid-tight separation chamber.

The method of the present invention comprises pumping a solution of mixed ampholytes through the flow channel while utilizing the thermal masses to create a temperature and corresponding pH gradient along the length of the closely-spaced transverse channels. The electrodes are utilized in order to generate an electric field along the length of the transverse channels so that each ampholyte will migrate from the flow channel into the transverse channels to a position corresponding to its isoelectric point. The thermal masses are then manipulated so as to change the pH gradient and cause the separated ampholytes to reenter the flow stream at different times so as to be separately eluted and collected.

It is therefore an object of the present invention to provide an ampholyte separation method and apparatus that will facilitate the detection and recovery of the separated ampholytes.

It is another object of the present invention to provide an ampholyte separation method and apparatus that will minimize the separation process time by utilizing a readily established and easily controllable pH gradient in free buffer solution.

It is still another object of the present invention to provide an ampholyte separation method and apparatus that will allow for the analysis of relatively large samples of mixed ampholytes.

DESCRIPTION OF THE DRAWINGS

Some of the objects of the invention having been stated, other objects will become evident as the description proceeds, when taken in connection with the accompanying drawings, in which:

FIG. 3 is an end elevation view of the separation apparatus of the invention.

BEST MODE FOR CARRYING OUT THE INVENTION

Figure 1:
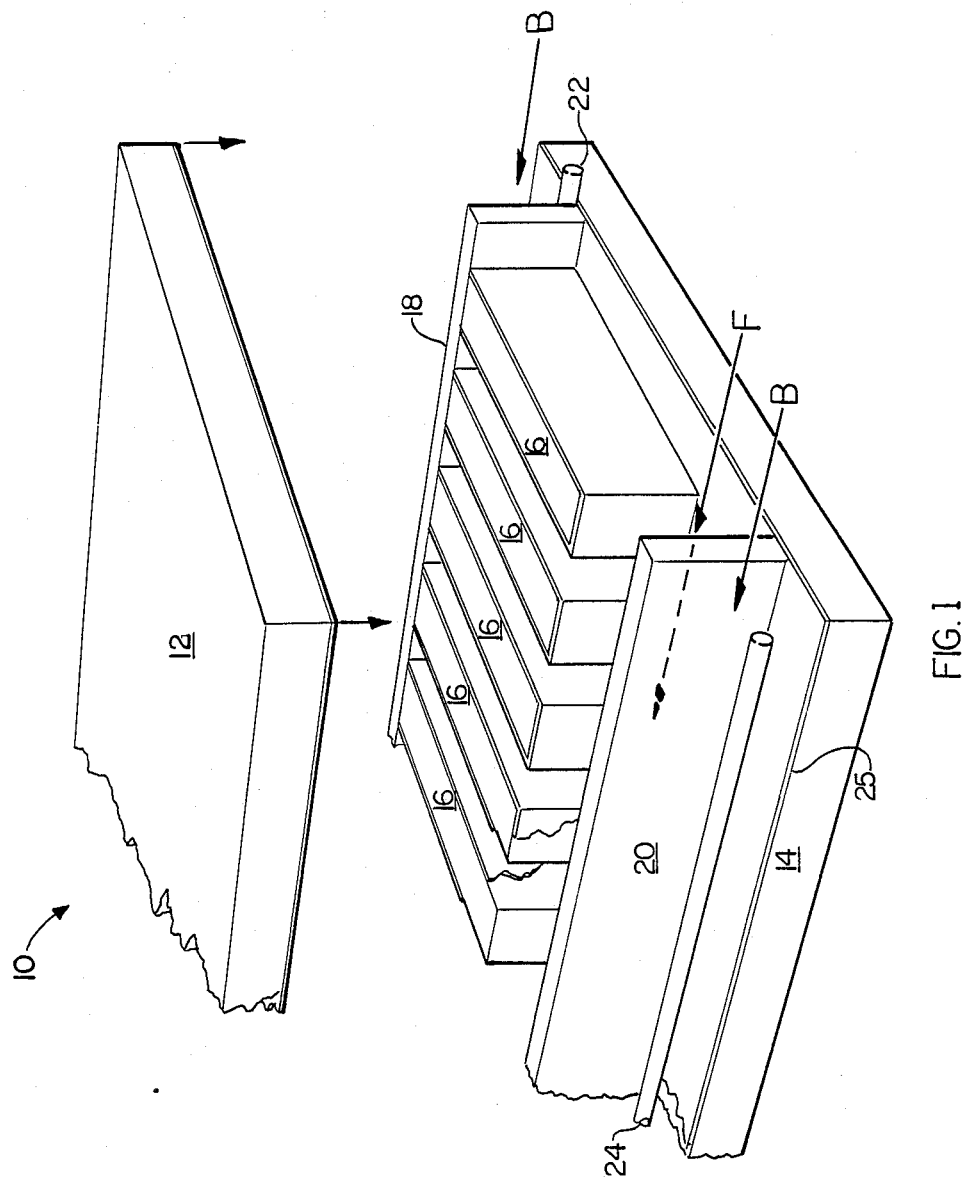
FIG. 1 is a perspective view taken of a section along the length of the separation apparatus of the invention with the top plate removed for clarity of illustration.
Figure 2:
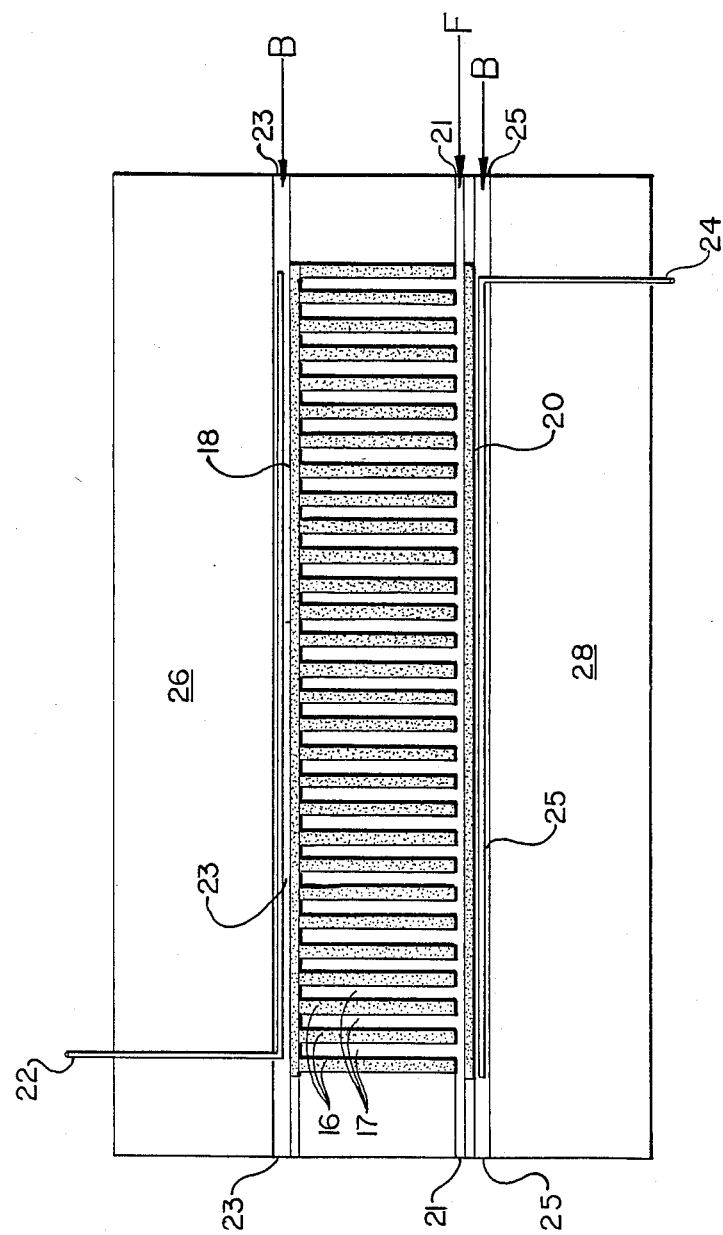
FIG. 2 is a top plan view of the separation apparatus of the invention with the top plate removed for clarity of illustration.

Referring now more specifically to the drawings, a preferred embodiment of an ampholyte separation apparatus according to the present invention is shown in FIGS. 1–3. More specifically, FIG. 1 is a perspective view of a section 10 taken from the medial portion of the separation apparatus. Section 10 comprises an upper plate 12 and a lower plate 14 with lower plate 14 having transverse barriers 16 which form closely-spaced channels 17 therebetween (see FIG. 2). A semipermeable membrane 18 extends along and abuts the ends of transverse barriers 16 while a semipermeable membrane 20 extends along and is spaced-apart from the other ends of transverse barriers 16. The space between semipermeable membrane 20 and the ends of transverse barriers 16 defines a sample flow channel 21 (see FIGS. 2 and 3) through which the sample to be separated is directed as shown by F. A fully permeable membrane (not shown) may be placed along the ends of transverse barriers 16 defining flow channel 21 in order to streamline sample flow F and to minimize turbulence within transverse channels 17.

It should be noted that the semipermeable membranes and transverse barriers can be arranged in various configurations so as to allow for different positioning of the flow channel. For example, both semipermeable membranes may be spaced-apart from both ends of the transverse barriers so as to create a flow channel at both ends of the transverse barriers. Alternatively, the semipermeable membranes may abut both ends of the transverse barriers with a flow channel extending parallel to the membranes and through the middle portion of the transverse barriers.

As shown clearly in FIGS. 2 and 3, semipermeable membrane 18 and semipermeable membrane 20 define compartments or channels wherein electrodes are positioned. Specifically, a cathode 22 is contained within an electrode compartment 23 such that cathode 22 is separated from transverse barriers 16 and transverse channels 17 by semipermeable membrane 18. Likewise, an anode 24 is contained within an electrode compartment 25 such that anode 24 is separated from sample flow channel 21 by semipermeable membrane 20. During the separation process, a solution of buffer is passed through electrode compartments 23 and 25 as shown by B.

A thermal mass 26 (see FIGS. 2 and 3) is positioned adjacent to anode compartment 23 and may be integral with lower plate 14. Similarly, a thermal mass 28 is positioned adjacent cathode compartment 25 and may be integral with the other side of lower plate 14. Thermal mass 26 and thermal mass 28 have independent temperature control means 27 and 29, respectively, so that each thermal mass can be maintained at a desired temperature.

Although thermal masses 26 and 28 are shown as the preferred means of creating a temperature gradient, it should be understood that any type of controllable heat source may be utilized in the instant invention to create the necessary temperature gradient. For example, a water bath/heat exchanger or a thermoelectric Peltier-effect cooler may be used in order to create a temperature gradient along the transverse channels.

The separation apparatus of the present invention can be constructed of any material having sufficient heat transfer properties such as copper, silver, gold, silicon, ceramic materials or other heavy metals. Upper plate 12 and lower plate 14 are preferably constructed of copper, and transverse barriers 16 are preferably an integral part of lower plate 14. Thermal mass 26 and thermal mass 28 may also be constructed of any material having sufficient heat transfer properties and are also preferably composed of copper.

The surfaces of the apparatus that come into contact with the solution of ampholytes and/or buffer are preferably coated with a layer of plastic or the like so as to insulate the surface from the electric field. The insulating material maintains the electric field within the solution and prevents dissipation of the electric field through the body of the apparatus. The insulating material may be any material that will sufficiently insulate the body of the apparatus from the electric field and that can be readily adhered to the surface of the apparatus. Polymers such as polyethylene, polyvinyl chloride and polypropylene are particularly useful as insulating materials with polyethylene being the preferred insulating material. Other insulating materials well known within the art such as Teflon tape and the like may also be utilized. The insulating material should be sufficiently hydrophilic so as to prevent protein adsorption into the insulating material. Insulating materials not having sufficient hydrophilicity may be treated with compounds such as acrylamide, polyethylene oxide, polyvinyl alcohols and the like. Acrylamide grafted onto a polyethylene coating is a particularly useful surface for the apparatus of the present invention.

Semipermeable membranes 18 and 20 may be constructed of any semipermeable material well known within the art that is permeable to small ions and buffer molecules but not to larger ampholyte molecules. The molecular weight cutoff of the membrane can be selected according to the molecular weights of the particular ampholytes and buffer solutions utilized. Cellulose acetate and commercially available dialysis membranes may be utilized as semipermeable membranes in the present invention. Cathode 22 and anode 24 may be constructed of any inert conducting material such as platinum, gold or carbon fibers and are preferably constructed of platinum.

In operation, the method of separation is carried out by pumping a solution of mixed ampholytes (or a solution containing a single ampholyte if concentration of the ampholyte is desired) through sample flow channel 21 while simultaneously utilizing cathode 22 and anode 24 24 to create an electric field transverse to the flow of the solution. A pH gradient is also established across the flow of solution and along the length of transverse channels 17 by maintaining thermal mass 26 and thermal mass 28 at different temperatures by independent temperature control means 27 and 29. The utilization of an appropriate buffer solution in flow channel 21, transverse channels 17 and electrode compartments 23 and 25 will not only provide the conductivity necessary for the electric field but will also allow the temperature gradient to set up a corresponding pH gradient since the hydrogen ion activity of the buffer solution is dependent upon temperature. The buffer solution is continually pumped through electrode compartments 23 and 25 as shown by B in FIG. 1 so as to flush the electrodes of any electrolysis products that may be produced during the separation process. Buffers suitable for establishing the pH gradient include tris(hydroxymethyl)aminomethane-HCl (commonly known as tris-HCl), phosphate buffers and acetate buffers with tris-HCl being the preferred buffer.

A pH gradient is selected according to the isoelectric points of the ampholytes such that the specific ampholytes to be separated will migrate from flow channel 21 into transverse channels 17 and stabilize at positions corresponding to their isoelectric points. Ampholytes having isoelectric points beyond semipermeable membrane 18 will stabilize at the boundary defined by membrane 18. The temperatures of thermal masses 26 and 28 are then changed so as to alter the pH gradient and cause the separated ampholytes to reenter the stream of sample flow F and be eluted at different times and thus allow for separate collection of each ampholyte. This method can also be utilized to increase the concentration of a single ampholyte in solution.

Alternatively, the pH gradient may be selected such that one or more ampholytes will remain in the sample flow channel 21 while one or more selected ampholytes will be drawn into transverse barriers 17 so as to separate the one or more selected ampholytes from the one or more ampholytes remaining in flow channel 21. The ampholyte(s) remaining in flow channel 21 would be collected and then the pH gradient manipulated so as to cause the selected ampholyte(s) to reenter the stream of sample flow F at different times and thus to be separately collected.

Applicant also contemplates that the apparatus of the present invention can be used to separate two ampholytes having equal isoelectric points but different mobilities. This technique would be executed by having a sufficiently long flow channel such that the different mobilities of each ampholyte would cause the ampholytes having different mobilities to migrate into different transverse barriers such that upon reentry into the flow stream F the ampholytes would be sufficiently spaced-apart to allow for the collection of each ampholyte at a different time.

As stated above, the semipermeable membranes and transverse barriers may be arranged in various configurations to selectively position the flow channel. Appropriate manipulations of the pH gradient in these various configurations will provide for much flexibility in carrying out the process steps. For example, if the semipermeable membranes are spaced-apart from both ends of the transverse barriers so as to create a flow channel along both ends of the transverse barriers, an ampholyte solution may be passed down the first flow channel and the pH gradient manipulated so as to cause the ampholytes to migrate through the transverse channels so as to enter the second flow channel at different times and to be separately eluted and collected.

Alternatively, if the semipermeable membranes abut both ends of the transverse barriers, an ampholyte solution may be directed through a flow channel in the middle portion of the barriers and the pH gradient manipulated so as to cause the ampholytes to migrate out of either side of the flow channel into the transverse channels. The pH gradient may then be manipulated so as to cause the ampholytes on either side of the flow channel to reenter the flow channel at different times and to be separately eluted and collected. Again, any ampholytes having an isoelectric beyond the semipermeable membrane boundaries will be forced against the membrane wall until the pH gradient is altered to cause the ampholytes to migrate back towards the flow channel.

Although it is preferable to remove the stabilized ampholytes from the transverse channels by manipulating the pH gradient as described above, in some instances it may be desirable to simply direct a flow of buffer solution through the transverse channels in order to flush the separated ampholytes into a flow channel to be separately eluted. One method of carrying out this flushing process involves blocking off one end of an electrode compartment so as to cause the buffer flow to pass through the semipermeable membrane into the transverse channels. In this manner, the separated ampholytes are forced into the flow channel at different times so as to be separately eluted and collected.

The inventive apparatus can also be utilized without a pH gradient in order to carry out an electrophoretic separation. Such an electrophoretic separation is carried out by inactivating the thermal masses 26 and 28 in FIG. 1 and passing a solution of mixed ampholytes having different electrophoretic mobilities through sample flow channel 21. Cathode 22 and anode 24 are utilized to create an electric field transverse to the flow of the solution so as to cause the ampholytes to migrate from flow channel 21 into transverse channels 17 and then through transverse channels 17 to semi-permeable membrane 18 where the ampholytes stabilize at the boundary defined by semi-permeable membrane 18. The electric field is then reversed and the ampholytes migrate at different speeds back towards sample flow channel 21. The ampholytes will therefore reach the sample flow channel at different times and be separately eluted. A similar electrophoretic process may be carried out utilizing the configuration referred to above having a flow channel in the middle portion of the transverse barriers.

An electrophoretic separation may also be carried out utilizing the configuration referred to above having a flow channel along both ends of the transverse barriers. An electrophoretic separation in this dual-channel configuration is carried out by passing an ampholyte solution down the first flow channel and utilizing the electric field to cause the ampholytes to migrate through the transverse barriers towards the second flow channel at different speeds so as to enter the second flow channel at different times and to be separately eluted and collected.

The electrophoretic separations described above do not require the establishment of a pH gradient and therefore the present invention also contemplates an apparatus designed without thermal masses or other means for establishing a pH gradient. For example, in FIG. 1, the thermal masses 26 and 28 would simply act as boundaries for electrode compartments 23 and 25 and no means for controlling the temperature of the thermal masses would be provided.

The present invention provides a thermally engendered pH gradient in combination with a novel arrangement of transverse barriers, flow channel, electrodes and semi-permeable membranes in order to more rapidly and efficiently separate ampholytes from a solution than has been known heretofore. The present separation apparatus is readily adaptable to commercial scale-up and can separate ampholytes having nearly equal isoelectric points. The invention eliminates long and tedious pH gradient preparations and allows for the efficient detection and recovery of the separated ampholytes and thereby overcomes the shortcomings inherent in presently known ampholyte separation techniques and devices.

It will thus be understood that the various details of the invention may be changed without departing from the scope of the invention. Furthermore, the foregoing description is for the purpose of illustration only, and not for the purpose of limitation—the invention being defined by the following claims.

What is claimed is:

1. An ampholyte separation apparatus comprising:
   a lower base plate;
   an upper base plate;
   at least two transversely extending barriers positioned between said upper and lower base plates and defining at least one transversely extending channel therebetween;
   a first semipermeable membrane abutting one end of each of said at least two transverse barriers;
   a second semipermeable membrane adjacent to and spaced-apart from the other end of each of said at least two transverse barriers so as to define a sample flow channel therebetween in fluid communication with said at least one transversely extending channel;
   a first electrode adjacent to said first semipermeable membrane and separated from said transversely extending barriers by said first semipermeable membrane;
   a second electrode adjacent to said second semipermeable membrane and separated from said sample flow channel by said second permeable membrane;
   a first temperature controllable thermal mass positioned in proximity to said first electrode; and
   a second temperature controllable thermal mass positioned in proximity to said second electrode;
   whereby an electric field and a pH gradient may be established along the length of said at least two transverse barriers so as to cause ampholytes flowing through said sample flow channel to be forced into said at least one transversely extending channel to differential positions corresponding to the isoelectric points of the ampholytes.

2. An apparatus according to claim 1 wherein said upper and lower base plates, said at least two transverse barriers and said thermal masses comprise copper.

3. An apparatus according to claim 2 wherein said upper and lower base plates, said at least two transverse barriers and said thermal masses are coated with polyethylene.

4. An apparatus according to claim 3 wherein acrylamide is grafted onto said polyethylene coating.

5. An apparatus according to claim 1 wherein said semipermeable membranes comprise cellulose acetate.

6. An apparatus according to claim 1 wherein said first electrode is a cathode and said second electrode is an anode.

7. An apparatus according to claim 6 wherein said electrodes comprise platinum.

8. An ampholyte separation apparatus comprising:
   a lower copper base plate;
   an upper copper base plate;
   a plurality of transversely extending copper barriers positioned between said upper and lower base plates and defining a plurality of transversely extending channels therebetween;
   a first semipermeable membrane of cellulose acetate extending along the length of said base plates and abutting one end of each of said transverse barriers;
   a second semipermeable membrane of cellulose acetate extending along the length of said base plates and being spaced-apart from the other end of each of said transverse barriers so as to define a sample flow channel therebetween in fluid communication with said transversely extending channels;
   a platinum cathode extending along and parallel to said first semi-permeable membrane and being separated from said transverse barriers by said first semi-permeable membrane;
   a platinum anode extending along and parallel to said second semi-permeable membrane and being separated from said flow channel by said second semi-permeable membrane;

a first copper-thermal mass positioned adjacent said cathode, said first copper thermal mass having an independent temperature control means; and a second copper thermal mass positioned adjacent said anode, said second copper thermal mass having an independent temperature control means;

whereby an electric field and a pH gradient may be established along the length of said transverse barriers so as to cause ampholytes traveling through said flow channel to be forced into said transversely extending channels to differential positions corresponding to the isoelectric points of the ampholytes.

9. An ampholyte separation apparatus comprising: at least two elongate barriers defining at least one elongate channel therebetween;

a first semi-permeable membrane positioned transverse to said at least two elongate barriers and adjacent to one end of each of said at least two elongate barriers;

a second semi-permeable membrane positioned transverse to said at least two elongate barriers and adjacent to the other end of each of said at least two elongate barriers;

means for creating an electric field along the length of said at least two elongate barriers, said means for creating an electric field being positioned adjacent to said semi-permeable membranes so as to be separated from said elongate barriers by said semi-permeable membranes; and at least one flow channel extending substantially parallel to said semi-permeable membranes and substantially transverse to said at least two elongate barriers.

10. An ampholyte separation apparatus comprising:

at least two elongate barriers defining at least one elongate channel therebetween;

a first semi-permeable membrane positioned transverse to said at least two elongate barriers and adjacent to one end of each of said at least two elongate barriers;

a second semi-permeable membrane positioned transverse to said at least two elongate barriers and adjacent to the other end of each of said at least two elongate barriers;

means for creating an electric field along the length of said at least two elongate barriers, said means for creating an electric field being positioned adjacent to said semi-permeable membranes so as to be separated from said elongate barriers by said said semi-permeable membranes;

at least one flow channel extending substantially parallel to said semi-permeable membranes and substantially transverse to said at least two elongate barriers; and means for thermally establishing and controlling a pH gradient along the length of said at least two elongate barriers.

11. A process for separating ampholytes comprising:

directing a solution containing one or more ampholytes through a flow channel which is transverse to at least two elongate barriers defining at least one elongate channel therebetween;

establishing an electric field along the length of said elongate barriers;

thermally engendering a pH gradient along the length of said elongate barriers so as to cause at least one of the ampholytes to migrate from the flow channel into said at least one elongate channel and stabilize at a position corresponding to the isoelectric point of the at least one ampholyte; and altering the pH gradient so as to cause the at least one ampholyte stabilized in said at least one elongate channel to reenter said flow channel and to be eluted and separately collected.

12. A process according to claim 11 wherein the pH gradient is thermally engendered so as to cause all of the ampholytes in solution to migrate into said at least one elongate channel and to stabilize at positions corresponding to their isoelectric points and wherein the pH gradient is altered so as to cause the ampholytes to reenter said flow channel at different times and to be separately eluted and collected.

13. A process according to claim 11 wherein the pH gradient is thermally engendered so as to cause one or more selected ampholytes to migrate into said at least one elongate channel and stabilize at positions corresponding to their isoelectric points while the other ampholytes remain in said flow channel so as to be eluted, and wherein the pH gradient is altered so as to cause the one or more selected ampholytes to reenter said flow channel at different times and to be separately eluted and collected.

14. A process for separating ampholytes comprising:

directing a solution containing two or more ampholytes through a flow channel which is transverse to a plurality of elongate barriers, said elongate barriers defining a plurality of elongate channels;

providing a first electrode adjacent one end of the transverse barriers and extending in the direction of the flow channel, said first electrode being separated from the transverse barriers by a first semi-permeable membrane which abuts the one end of said transverse barriers;

providing a second electrode spaced-apart from the other end of the transverse barriers and extending in the direction of the flow channel, said second electrode being separated from the transverse barriers by a second semi-permeable membrane which is also spaced-apart from the other end of the transverse barriers and is adjacent to the flow channel;

generating an electric field along the length of the transverse barriers with the first and second electrodes;

providing a first temperature controllable thermal mass adjacent to said first electrode so that said first electrode is positioned between said first semi-permeable membrane and said first thermal mass;

providing a second temperature controllable thermal mass adjacent to said second electrode so that said second electrode is positioned between said second semi-permeable membrane and said second thermal mass;

thermally engendering a pH gradient along the transverse barriers with the first and second thermal masses so as to cause at least one of the ampholytes to migrate from the flow channel into the elongate channels and stabilize at a position corresponding to the isoelectric point of the at least one ampholyte; and altering the pH gradient so as to cause the at least one ampholyte stabilized in the elongate channels to reenter the flow channel and to be eluted and separately collected.

15. A process according to claim 14 wherein said flow channel, said transverse barriers and said thermal masses comprise copper.

16. A process according to claim 15 wherein said flow channel, said transverse barriers and said thermal masses are coated with polyethylene.

17. A process according to claim 16 wherein acrylamide is grafted onto said polyethylene coating.

18. A process according to claim 14 wherein the semi-permeable membranes comprise cellulose acetate.

19. A process according to claim 14 wherein the first electrode is a cathode and the second electrode is an anode.

20. A process according to claim 19 wherein the electrodes comprise platinum.

21. A process according to claim 14 wherein the pH gradient is thermally engendered so as to cause all of the ampholytes contained in the solution to migrate into the elongate channels and stabilize at positions corresponding to their isoelectric points and wherein the pH gradient is altered so as to cause the ampholytes to reenter the flow channel at different times and to be separately eluted and collected.

22. A process according to claim 14 wherein the pH is thermally engendered so as to cause one or more selected ampholytes to migrate into the elongate channels and stabilize at positions corresponding to their isoelectric points while the other ampholytes remain in the flow channel so as to be eluted and wherein the pH gradient is altered so as to cause the one or more selected ampholytes to reenter the flow channel at different times and to be separately eluted and collected.

23. A process for separating ampholytes comprising:
directing a solution containing two or more ampholytes with at least two of the ampholytes having identical isoelectric points but different mobilities through a flow channel which is transverse to a plurality of elongate barriers defining a plurality of elongate channels;
establishing an electric field along the length of said elongate barriers;
thermally engendering a pH gradient along the length of said elongate barriers so as to cause at least one of the ampholytes to migrate from the flow channel into the elongate channels and stabilize at a position corresponding to the isoelectric point of the at least one ampholyte and so as to cause the at least two ampholytes having identical isoelectric points but different mobilities to migrate into different elongate channels due to the different mobilities of the at least two ampholytes; and
altering the pH gradient so as to cause the at least one ampholyte to reenter the flow channel and to be separately eluted and collected and so as to cause the at least two ampholytes having identical isoelectric points to reenter the flow channel at different positions along the flow channel due to their location in different elongate channels and to also be separately eluted and collected.

24. A process for separating ampholytes comprising:
directing a solution containing one or more ampholytes through one of one or more flow channels which are transverse to at least two elongate barriers which define at least one elongate channel between said barriers;
establishing an electric field along the length of said elongate barriers so as to cause at least one of the ampholytes to migrate at a speed according to its electrophoretic mobility from said one of one or more flow channels through said at least one elongate channel and into one of the one or more flow channels to be eluted and separately collected.

25. A process for separating ampholytes comprising:
directing a solution containing one or more ampholytes through one of one or more flow channels which are transverse to at least two elongate barriers defining at least one elongate channel therebetween;
establishing an electric field along the length of said elongate barriers;
thermally engendering a pH gradient along the length of said elongate barriers so as to cause at least one of the ampholytes to migrate from the flow channel into said at least one elongate channel; and
altering the pH gradient so as to cause the at least one ampholyte in said elongate channel to enter one of said one or more flow channels and to be eluted and separately collected.

26. A process for separating ampholytes comprising:
directing a first solution containing one or more ampholytes through one of one or more flow channels which are transverse to at least two elongate barriers defining at least one elongate channel therebetween;
establishing an electric field along the length of said elongate barriers;
thermally engineering a pH gradient along the length of said elongate barriers so as to cause at least one of the ampholytes to migrate from the flow channel into said at least one elongate channel; and
flushing a second solution through the transverse channels so as to cause the at least one ampholyte in said elongate channel to enter one of said one or more flow channels and to be eluted and separately collected.

27. A process for separating ampholytes comprising:
directing a solution containing one or more ampholytes through a flow channel which is transverse to at least two elongate barriers defining at least one elongate channel therebetween, said two elongate barriers having a semi-permeable membrane abutting the ends of said elongate barriers opposite said flow channel;
establishing an electric field along the length of said elongate barriers so as to cause at least one of the ampholytes to migrate from the flow channel into said at least one elongate channel and stabilize at the boundary defined by said semipermeable membrane; and
reversing the electric filed so as to cause the at least one ampholyte stabilized at said boundary to migrate through said at least one elongate channel towards said flow channel at a speed according to the electrophoretic mobility of the ampholyte and to reenter said flow channel to be eluted and separately collected.

* * * * *